US006300106B1

(12) United States Patent
Caille

(10) Patent No.: US 6,300,106 B1
(45) Date of Patent: Oct. 9, 2001

(54) METHOD OF PREPARING 3-[2-{(METHYLSULFONYL)OXY}-ETHOXY ]-4-(TRIPHENYLMETHOXY)-1-BUTANOL, METHANE SULFONATE

(75) Inventor: Jean-Claude Caille, Angers (FR)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 09/718,711

(22) Filed: Nov. 22, 2000

(51) Int. Cl.$^7$ ............... C12P 17/06; C12P 11/00; C12N 9/54; C07D 315/00
(52) U.S. Cl. .............. 435/125; 435/221; 435/130; 549/423
(58) Field of Search ................... 435/130, 221, 435/125; 549/423

(56) References Cited

U.S. PATENT DOCUMENTS 5,157,133 * 10/1992 Chabardes et al. ............. 549/423
5,721,272 * 2/1998 Faul et al. ...................... 514/450
6,117,861 * 9/2000 Engel et al. ..................... 514/183

FOREIGN PATENT DOCUMENTS

WO 97/19080    5/1997  (WO) .

OTHER PUBLICATIONS

M. M. Faul et al., "Macrocyclic Bisindolylmaleimides: Synthesis by Inter– and Intramolecular Alkylation", *Journal of Organic Chemistry*, vol. 63, No. 6, pp. 1961–1973 (1998).

Y–F. Wang et al., "Lipase–Catalyzed Irreversible Transesterifications Using Enol Esters as Acylating Reagents: Preparative Enantio– and Regioselective Syntheses of Alcohols, Glycerol Derivatives, Sugars, and Organometllics", *Journal of the American Chemical Society*, vol. 110, No. 21, pp. 7200–7205 (1988).

M. Johannsen et al., "Asymmetric Hetero Diels–Alder Reactions and Ene Reactions Catalyzed by Chiral Copper (II) Complexes", *Journal of Organic Chemistry*, vol. 60, No. 18, pp. 5757–5762 (1995).

A. Lubineau et al., "Aqueous Hetero Diels–Alder Reactions: The Carbonyl Case.", *Tetrahedron*, vol. 50, No. 34, pp. 10265–10276 (1994).

* cited by examiner

Primary Examiner—Herbert J. Lilling
(74) Attorney, Agent, or Firm—Dennis G. Millman

(57) ABSTRACT

A method of producing (S)-3-[2-{(methylsulfonyl)oxy}ethoxy]-4-(triphenylmethoxy)-1-butanol methane sulfonate using 1,3-butadiene and a ketoethanal to form an intermediate racemic mixture. The racemic mixture is resolved to remove one isomer from the reaction product mixture. Following resolution, the following steps are performed: reduce the isomer to an alcohol, react the alcohol with triphenylmethyl chloride, ozonalyze the resulting reaction product, reduce the ozonalyzed product to yield a diol and react the diol with a methane sulfonyl compound to form (S)-3-[2-{(methylsulfonyl)oxy}ethoxy]-4-(triphenylmethoxy)-1-butanol methane sulfonate. Alternatively, the racemic mixture may first be reduced and the resulting racemic alcohol mixture is resolved to isolate one isomer of the alcohol and the remaining process steps are followed.

24 Claims, No Drawings

METHOD OF PREPARING 3-[2-{(METHYLSULFONYL)OXY}-ETHOXY]-4-(TRIPHENYLMETHOXY)-1-BUTANOL, METHANE SULFONATE

BACKGROUND OF THE INVENTION

1. Field of the Invention

The present invention relates to the production of 3-[2-{(methylsulfonyl)oxy}ethoxy]-4-(triphenylmethoxy)-1-butanol methane sulfonate, more particularly to the preparation of a single optical isomer of the product involving the resolution of a racemic mixture of intermediate products.

2. Prior Art

The production of certain pharmaceuticals involves the use 3-[2-{(methylsulfonyl)oxy}ethoxy]-4-(triphenylmethoxy)-1-butanol methane sulfonate (MTBS). Related compounds to MTBS are disclosed in PCT Publication No. WO 97/19080. Preparation of MTBS and related compounds has traditionally involved using relatively expensive starting materials. Some of these methods are described in Journal of Organic Chemistry, Vol. 63, No. 6, pp. 1961–1973 (1998) and one synthesis route is shown in the following reaction scheme. In this synthesis technique, (R)-glycidol (graphic formula A) is protected with triphenylmethyl (Tr) to yield trityl glycidol (graphic formula B), and the glycidol ring is opened by treatment with vinylmagnesium bromide to produce the ether of graphic formula C. Allylation of compound C produces the ether of graphic formula D. Ozonolysis of compound D followed by subsequent sodium borohydride reduction yields the diol of graphic formula E which is treated with methane sulfonyl chloride (MsCl) to produce (S)-3-[2-{(methylsulfonyl)oxy}ethoxy]-4-(triphenylmethoxy)-1-butanol methane sulfonate (graphic formula F).

SUMMARY OF THE INVENTION

This need is met by the method of the present invention according to which the S-isomer or R-isomer of (3,6-dihydro-2H-pyran-2-yl)-methanol is formed via a process which produces a racemic mixture of intermediate reaction products. The racemic mixture is resolved to selectively isolate the desired isomer of the alcohol. The desired isomer of the alcohol is then further reacted to yield 3-[2-(methylsulfonyl)oxy}ethoxy]-4-(triphenylmethoxy)-1-butanol methane sulfonate.

The method of the present invention includes the steps of:
(a) reacting 1,3-butadiene with a ketoethanal to form a racemic mixture of a 2-carbonyl-3,6-dihydropyran compound; and
(b) converting the 2-carbonyl-3,6-dihydropyran compound to one isomer of (3,6-dihydro-2H-pyran-2-yl)-methanol.

The method further includes a step of enzymatically resolving the racemic mixture of the dihydropyran derivative produced in step (a) to isolate one isomer of the dihydropyran of step (a) in between steps (a) and (b). Alternatively, the racemic mixture may be converted to a racemic mixture of the alcohol of step (b) and the resulting racemic mixture of the 2-carbonyl-3,6-dihydropyran compound is chemically or enzymatically resolved to isolate the desired isomer of (3,6-dihydro-2H-pyran-2-yl)-methanol A preferred method of isolating the desired isomer of the 2-carbonyl-3,6-dihydropyran compound of step (a) includes reacting the racemic mixture with a hydrolase, preferably a protease, more preferably a *Bacillus lentus* protease. The isomers of the dihydropyran derivative are selectively hydrolyzed to a carboxylic acid by reaction with the hydrolase creating an aqueous phase containing one isomer and an organic phase containing the other isomer. The organic and

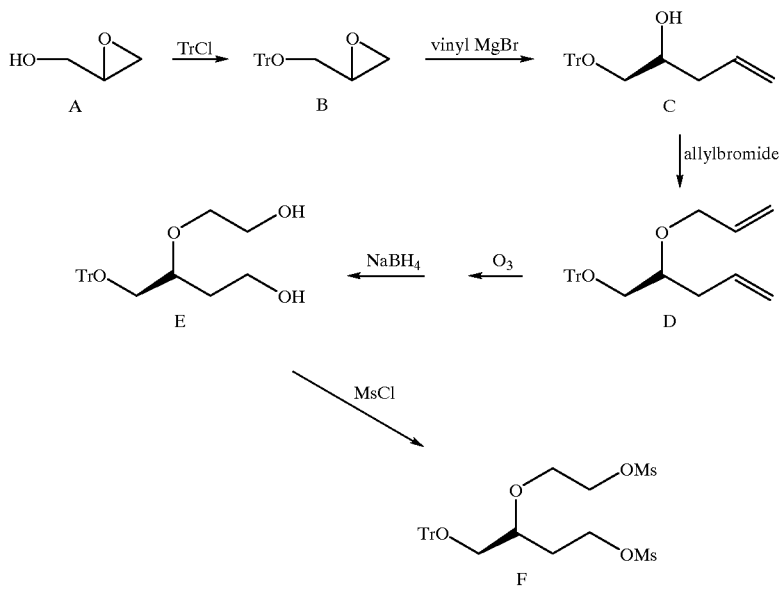

This method of producing MTBS is not commercially economical. Accordingly, a need remains for preparing 3-[2-(methylsulfonyl)oxy}ethoxy]-4-(triphenylmethoxy)-1-butanol methane sulfonate which uses readily available and relatively inexpensive starting materials.

aqueous phases are separated from each other to yield an enantiomeric pure mixture comprising the desired isomer. The reduction step (b) preferably includes reacting the dihydropyran derivative with lithium aluminum hydride to form an alcohol.

The R- or S- isomer of (3,6-dihydro-2H-pyran-2-yl)-methanol may be further treated to produce 3-[2-(methylsulfonyl)oxy}ethoxy]-4-(triphenylmethoxy)-1-butanol methane sulfonate by the additional steps of:

(c) reacting the alcohol with triphenylmethyl chloride to form a triphenylmethoxy-substituted 3,6-dihydropyran;

(d) ozonolyzing the triphenylmethoxy-substituted 3,6-dihydropyran to form a reaction product;

(e) reducing the reaction product to form a diol; and (f) reacting the diol with a methanesulfonyl compound to form an isomer of 3-[2-{(methylsulfonyl)oxy}ethoxy]-4-(triphenylmethoxy)-1-butanol, methane sulfonate.

Step (c) may include adding a catalyst to the alcohol. In step (d), ozone preferably is bubbled through a solution of the triphenylmethoxy-substituted 3,6-dihydropyran to produce an ozonated solution which is immediately reduced in step (e) without separation by adding a reducing agent such as sodium borohydride to the ozonated solution.

DETAILED DESCRIPTION OF THE INVENTION

The method of the present invention includes following the steps depicted in Reaction A followed by Reactions B or C to produce an isomer of (3,6-dihydro-2H-pyran-2-yl)-methanol and optionally following the steps of Reaction D to produce an isomer of 3-[2 -{(methylsulfonyl)oxy}ethoxy]-4-(triphenylmethoxy)-1-butanol, methane sulfonate.

In Reaction A, 1,3-butadiene represented by graphic formula I is reacted with a ketoethanal represented by graphic formula II wherein $R_1$ represents a hydroxyl group, a linear or branched $C_1$–$C_{12}$ alkoxy group, an unsubstituted or $C_1$–$C_{12}$ alkyl substituted phenoxy group, or the group —$NR_2R_3$ where $R_2$ and $R_3$ are the same or different and are hydrogen or $C_1$–$C_{12}$ alkyl or $R_2$ and $R_3$ are joined together to form a 2 to 12 membered ring with one or more of the cyclic atoms being a heteroatom. A preferred heteroatom is the sulfur of a sulfonyl group. Preferably, $R_1$ is a hydroxyl or $C_1$–$C_{12}$ alkoxy group. Compounds I and II are dissolved in a suitable solvent such as toluene with a stabilizer such as hydroquinone and heated in an autoclave to produce a racemic mixture of the compound of graphic formula III. The racemic mixture of compound III may be purified by distillation or a similar technique.

Reaction A

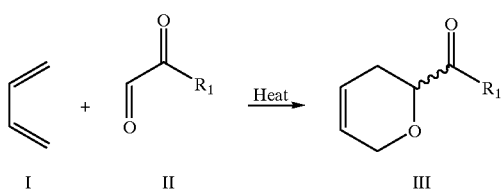

In Reaction B, where $R_1$ is not a hydroxyl group, the enantiomers of graphic formula III are separated by enzyme resolution. The compounds of graphic formula III are treated with a hydrolase such as an aqueous solution of *Bacillus lentus* protease yielding an aqueous phase containing the R-isomer of 3,6-dihydropyran-2-carboxylic acid (not shown) and an organic phase of the desired S-isomer represented by graphic formula IV. Compound IV is separated from the aqueous phase and is reduced with a reducing agent such as lithium aluminum hydride or PMHS (polymethylhydrosiloxane) in a solvent such as tetrahydrofuran (THF) to produce (S)-(3,6-dihydro-2H-pyran-2-yl)-methanol represented by graphic formula V. Other suitable reducing agents include bis(2-methoxyethoxy)aluminum hydride, sodium borohydride and the like. Catalytic hydrogenation may also be used.

Reaction B

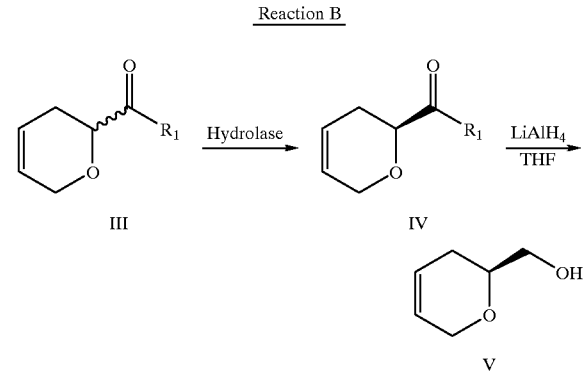

Alternate routes of producing an isomer of (3,6-dihydro-2H-pyran-2-yl)-methanol are shown in Reaction C. In Reaction C, compound III from Reaction A is reduced with a reducing agent such as lithium aluminum hydride in a solvent such as THF to produce a racemic mixture of the alcohol of compound Va. Compound Va is reacted with vinyl acetate or a similar compound represented by graphic formula VI (where $R_4$ is hydrogen or $C_1$–$C_6$ alkyl) in the presence of a lipase to produce the acetate ester represented by graphic formula VII and the alcohol of graphic formula V. This lipase-catalyzed reaction is described further in Journal of the American Chemical Society, Vol. 110, No. 21, pp. 7200–7205 (1988). Compound V is separated from compound VII by a conventional technique such as distillation or chromatography. Compound Va may also be chemically resolved to isolate one isomer thereof by treatment with a chemical resolving agent such as a chiral acid to produce the isomer of (3,6-dihydro-2H-pyran-2-yl)-methanol represented by compound V.

An alternative route may be used when compound III is an ester. The ester of compound III is hydrolyzed by a base or an acid to produce a racemic mixture of 3,6-dihydropyran-2-carboxylic acid represented by graphic formula VIII. Compound VIII is treated with a chemical resolving agent such as a chiral amine to yield an optically pure acid represented by graphic formula IX. Compound IX is reacted with an alcohol such as methanol or ethanol ($R_5OH$ where $R_5$ may be $C_1$–$C_6$ alkyl) to yield the ester represented by graphic formula X. Compound X is reduced, for example with lithium aluminum hydride in THF, into the optically pure alcohol of graphic formula V.

In either Reaction B or Reaction C, the product is an isomer of (3,6-dihydro-2H-pyran-2-yl)-methanol represented by graphic formula V. Compound V is preferably the S-isomer thereof for further reaction in Reaction D. However, the R-isomer of (3,6-dihydro-2H-pyran-2-yl)-methanol may be produced by using the appropriate hydrolase or chemical resolving agent.

Reaction C

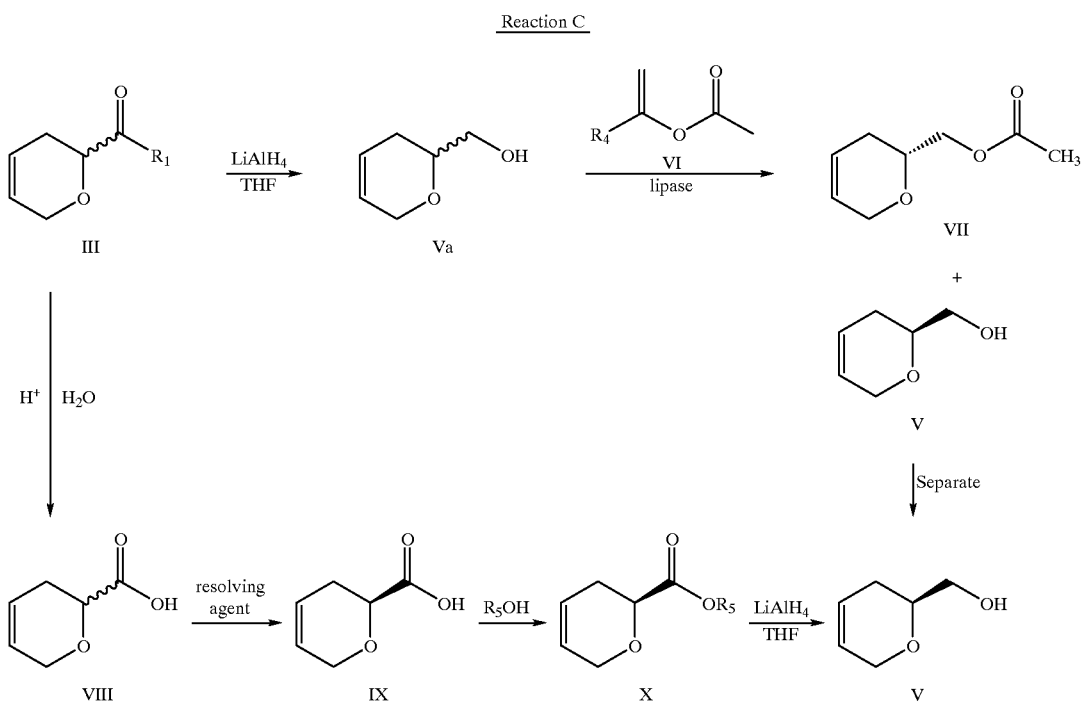

In Reaction D, the alcohol of graphic formula V is reacted with triphenylmethyl chloride (TrCl) in a suitable solvent such as methylene chloride and triethylamine (TEA), optionally with a catalyst such as 4-dimethyl amino pyridine (DMAP) to yield (S)-trityl-(3,6-dihydro-2H-pyran-2-yl)-methyl ether represented by graphic formula XI. Compound XI is dissolved in a solvent such as methylene chloride and methanol. The solution is ozonated causing ozonolysis of the double bond in the ether of compound XI and the intermediates are directly reduced by adding the reaction mixture to a reducing agent such as sodium borohydride to yield the diol of (S)-3-(2-hydroxyethoxy)-4-(triphenylmethoxy)-1-butanol represented by graphic formula XII. Compound XII is reacted with methane sulfonyl chloride (MsCl) in a solvent such as methylene chloride in the presence of a base such as methyl amine to yield MTBS represented by graphic formula XIII.

A key advantage of the present invention is the ability to use relatively inexpensive and readily available starting materials namely, 1,3-butadiene and a ketoethanal to produce an isomer of (3,6-dihydro-2H-pyran-2-yl)-methanol and further convert the alcohol to MTBS.

Although the invention has been described generally above, the following example gives additional illustration of the process steps typical of the present invention.

EXAMPLE

Step 1

Ethyl glyoxylate in a 50 percent solution in toluene having 949.4 grams of solids was charged to a reaction vessel and agitated at 500 revolutions per minute. The reactor was purged with nitrogen and evacuated, and a 5 psig nitrogen pad was maintained on the reactor. 1,3-Butadiene Reaction D

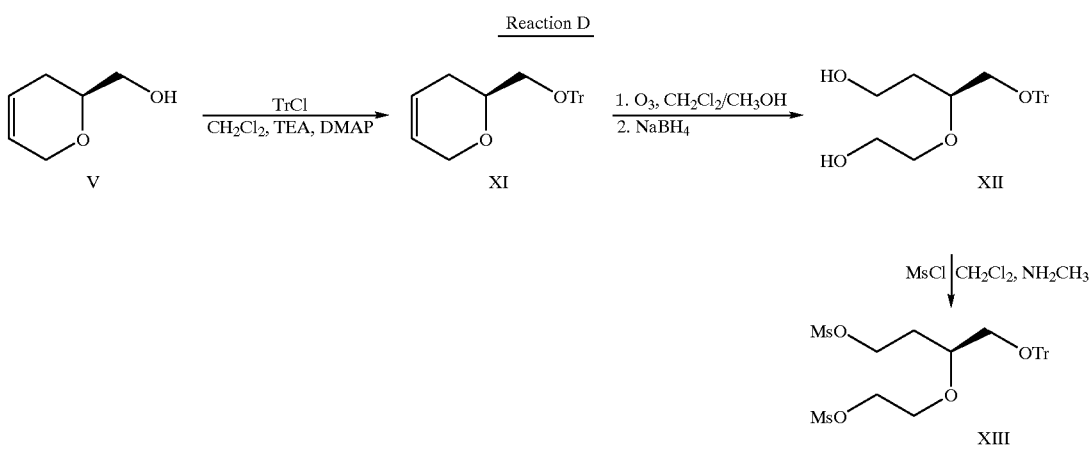

(439.3 grams) was added to the reactor, and the reaction mixture was heated to 160°C. The reaction was allowed to proceed for several hours until at least 95% of the ethyl glyoxylate was reacted as determined by gas chromatography. The reaction vessel was cooled to 40° C. and the vacuum was released. The reaction product was collected and vacuum distilled to yield a reaction product having a boiling point of 80° to 90° C. at 15 to 16 torr with a yield of 30–35%. The reaction product was determined to be a racemic mixture of 2-ethoxycarbonyl-3,6-dihydropyran.

Step 2

The racemic mixture of 2-ethoxycarbonyl-3,6-dihydropyran of step 1 (2.5 grams) was added to a reaction flask followed by additions of 7 milliliters (ml) of 0.2 M phosphate buffer (pH 7.5) and 2 ml of *Bacillus lentus* protease solution (approximately 50 milligrams per milliliter of protein). The reaction mixture was stirred at room temperature (23° C.) and the pH was maintained at 7.5 by the dropwise addition of sodium hydroxide. After 5 hours, the enantiomeric purity of the unreacted ester was 99 percent and the reaction was stopped by adding 10 ml methyl t-butyl ether (MTBE) yielding an aqueous phase and an organic phase. The pH of the aqueous phase was adjusted to 8.5 and the mixture was transferred to a separatory funnel. The aqueous phase was extracted twice with 20 ml MTBE, the separated organic layers were combined and extracted once with a saturated sodium bicarbonate solution (10 ml) and extracted once with a saturated sodium chloride solution (10 ml). The organic layer was dried over 2 grams of anhydrous magnesium sulfate. The solvent was removed under reduced pressure via a water aspirator using a rotary evaporator to provide 1.2 grams of a fragrant clear yellow liquid at 48 percent yield. Gas chromatography analysis and nuclear magnetic resonance (NMR) showed the product to have a structure consistent with (S)-2-ethoxycarbonyl-3,6-dihydropyran.

Step 3

A solution (260 ml) of lithium aluminum hydride (10.45 grams) in THF (9.88 grams) was charged to a one liter reactor under nitrogen and cooled to –2° C. A solution of 78 grams of the (S)-2-ethoxycarbonyl-3,6-dihydropyran produced as described in Step 2 in 75 ml of THF was added dropwise to the reaction flask over a period of 1.25 hours at 0–6° C. with stirring. After the addition of the isomer was complete, the mixture was stirred for about 2 hours while allowing the mixture to warm to about 12° C. Water was added dropwise (10 ml) followed by 10 grams of a 15 percent solution of sodium hydroxide. The mixture went through a thick gel phase and eventually broke apart. Water was again added (30 grams) over a period of 10 minutes. The mixture was stirred for an hour and filtered. The resulting solids were washed four times with about 50 ml THF. The final THF solution was stripped in a vacuum to constant weight yielding 52.0 grams of yellowish liquid. The composition of the reaction product was determined to have a structure consistent with (3,6-dihydro-2H-pyran-2-yl)-methanol.

Step 4

(3,6-dihydro-2H-pyran-2-yl)-methanol from Step 3 (46.06 grams) was added to a reaction flask containing a mixture of 117.23 grams trityl chloride, 250 ml methylene chloride and 54 ml TEA and stirred. The initial temperature was about 18° C. and rose to 44° C. over 5 minutes. The mixture was cooled down to room temperature and stirred for two days under nitrogen. The mixture was extracted twice with 200 ml of water, and the aqueous phase was discarded. The organic phase was dried over magnesium sulfate and stripped in a vacuum to remove the solvent (methylene chloride). Heptane (200 ml) was added and the mixture was stirred under vacuum while removing most of the methylene chloride. The heptane mixture was filtered and washed with heptane yielding 76 grams of crystals determined to be 90 percent pure via high pressure liquid chromatography (HPLC).

The mother liquor was concentrated to obtain a yellow syrup. Isopropanol was added (150 ml) and the mixture was stirred and allowed to stand for one half hour. The mixture was filtered and washed with isopropanol and dried to yield approximately 15 grams of solids. The two lots of solids were combined and heated to a boil in about 500 ml isopropanol. The solution was allowed to stand at room temperature and then cooled to about 15° C. to precipitate the crystals. The mixture was filtered and washed with cold isopropanol and dried to yield 78.6 grams of a solid. The remaining mother liquors were combined and stripped in a vacuum. TEA was added (5 ml) with 50 ml of isopropyl alcohol and the mixture was allowed to stand overnight at room temperature. The precipitate was filtered, washed and dried yielding 9.5 grams of a product. The product was recrystallized twice from about 5 ml/gram isopropanol to obtain 7 grams of product. The additional product was mixed with the main lot of crystals. A total yield was 85.6 grams of a solid having a structure consistent with (S)-trityl-(3,6-dihydro-2H-pyran-2-yl)-methyl ether.

Step 5

(S)-trityl-(3,6-dihydro-2H-pyran-2-yl)-methyl ether from Step 4 (71.5 grams) was dissolved in a mixture of 350 ml methylene chloride and 250 ml methanol. The solution was charged to a one liter jacketed reactor equipped with a gas filter inlet, thermocouple and dry ice condenser. The system was cooled to –40° C. with a circulating bath using a fluorinated liquid and dry ice. Ozonated air was bubbled through the solution for about 85 minutes until the solution turned blue, indicating the end of the reaction. The temperature during ozonation ranged from –40° to –25° C. HPLC showed the reaction to be complete.

Step 6

The reaction mixture of Step 5 was directly added into a reaction flask containing a solution of 17.5 grams sodium borohydride in 400 ml of 0.02 N sodium hydroxide with stirring. The mixture was stirred over night at room temperature. The mixture was stirred for another approximately 20 hours at room temperature. HPLC showed the reaction to be complete. The organic phase was separated and the aqueous phase was re-extracted with 50 ml methylene chloride. The organic phases were combined and stripped in a vacuum to obtain 81.8 grams of a viscous syrup. HPLC showed the syrup to include 96 percent of a product having a structure consistent with (S)-3-(2-hydroxyethoxy)-4-(triphenylmethoxy)-1-butanol.

Step 7

A solution of 81.9 grams of (S)-3-(2-hydroxyethoxy)-4-(triphenylmethoxy)-1-butanol from Step 6 in 800 ml methylene chloride was charged to a 2 liter round bottom flask equipped with a mechanical stirrer, thermocouple and additional funnel with a nitrogen sweep. The mixture was stirred and 87 ml TEA was added producing a clear colorless solution. The solution temperature increased from 21° C. to 23° C. and was cooled to 0–5° C. in an ice bath. A mixture of 43.5 ml methane sulfonyl chloride and 50 ml methylene chloride at 0–5° C. was added to the reaction flask over 80 minutes. Following complete addition, the reaction mixture was stirred for 1 hour at 0–5° C. The reaction mixture was diluted with 500 ml methylene chloride and extracted twice with 315 ml water and extracted once with 315 ml sodium bicarbonate. The organic phase was dried over about 100 grams sodium sulfate for 30 minutes and filtered. The solids were evaporated to dryness at room temperature at 15 mbar and dried at 10° C. overnight at 2 mbar yielding 111.1 grams of a crude product. The crude product was dissolved in 345 ml ethyl acetate at 35–40° C. The resulting solution was filtered via a Buechner funnel (150 ml, 60 M) on a filter disk. The filtrate was charged into a 2 liter round bottom flask equipped with a mechanical stirrer, thermocouple and additional funnel with a nitrogen sweep to which 690 ml heptane at 23° C. were added over 3.5 hours. Following complete heptane addition, the mixture was stirred for 90 minutes at room temperature. The solids were separated by filtration on a 1 liter pressure funnel for about 5 minutes yielding a clear filtrate. Residual solids in the reaction flask were washed out with two washes of the filtrate and mother liquor. The solids were compacted several times until no more filtrate was collected and were charged into the reaction flask with 300 ml heptane along with the filter cake. The heptane was removed via pressure filtration and the filter cake was compressed several times with a spatula. The solids were washed with 700 ml pentane, filtered and dried under nitrogen for 1 hour yielding 210 grams of wet solids. The mother liquor and the heptane from the washes were combined and evaporated to dryness at 15 mbar at room temperature yielding an additional 10.8 grams of a yellow-colored semi-solid. The solids were combined and dried at 2 mbar at 10° C. for 22 hours until a constant weight was obtained yielding 96.7 grams of a product having a structure determined to be consistent with (S)-3-[2-{(methylsulfonyl)oxy}ethoxy]-4-(triphenylmethoxy)-1-butanol, methane sulfonate.

It will be readily appreciated by those skilled in the art that modifications may be made to the invention without departing from the concepts disclosed in the foregoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

I claim:

1. A method of producing (S)-3-[2-{(methylsulfonyl)oxy}ethoxy]-4-(triphenylmethoxy)-1-butanol methane sulfonate comprising the steps of:
    a) reacting 1,3-butadiene with a ketoethanal compound to form a racemic mixture of a 2-carbonyl-3,6-dihydropyran compound;
    b) converting the 2-carbonyl-3,6-dihydropyran compound to (3,6-dihydro-2H-pyran-2-yl)-methanol;
    c) reacting the alcohol with triphenylmethyl chloride to form a solution comprising 2-triphenylmethoxy-3,6-dihydropyran;
    d) reacting the 2-triphenylmethoxy-3,6-dihydropyran with ozone to form a reaction product;
    e) reducing the reaction product to form a diol comprising 3-(2-hydroxyethoxy)-4-(triphenylmethoxy)-1-butanol; and
    f) reacting the diol with a methane sulfonyl compound to form 3-[2-{(methylsulfonyl)oxy}ethoxy]-4-(triphenylmethoxy)-1-butanol methane sulfonate,
    wherein the dihydropyran produced in step a) or the alcohol produced in step b) comprises a racemic mixture thereof and said method further comprises a step of resolving the racemic mixture such that the alcohol reacted in step c) consists of one isomer thereof.

2. The method of claim 1 wherein the resolving step is performed between steps a) and b).

3. The method of claim 1 wherein the resolving step is performed between steps b) and c).

4. The method of claim 2 wherein the resolving step comprises reacting the racemic mixture of the 2-carbonyl-3,6-dihydropyran compound with a hydrolase to produce a resolved product composition having an aqueous phase and an organic phase.

5. The method of claim 4 wherein the R-isomer of the racemic mixture is present in the aqueous phase and the S-isomer is present in the organic phase.

6. The method of claim 5 further comprising a step of separating the aqueous phase from the organic phase thereby removing the R-isomer from the resolved product composition.

7. The method of claim 4 wherein the hydrolase comprises a protease.

8. The method of claim 7 wherein the protease comprises a *Bacillus lentus* protease.

9. The method of claim 4 wherein step b) comprises reacting the 2-carbonyl-3,6-dihydropyran compound with lithium aluminum hydride.

10. The method of claim 1 wherein step c) further comprises adding a catalyst to the alcohol.

11. The method of claim 1 wherein step d) comprises dissolving the pyran into a solution and bubbling ozone through the solution to produce an ozonated solution.

12. The method of claim 11 wherein step e) comprises adding a reducing agent to the ozonated solution.

13. The method of claim 12 wherein the reducing agent comprises sodium borohydride.

14. The method of claim 1 wherein the ketoethanal compound may be represented by the following graphic formula

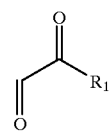

wherein $R_1$ represents a hydroxyl group, a linear or branched $C_1$–$C_{12}$ alkoxy group, an unsubstituted or $C_1$–$C_{12}$ alkyl substituted phenoxy group, or —$NR_2R_3$ where $R_2$ and $R_3$ are the same or different and are each hydrogen or $C_1$–$C_{12}$ alkyl or $R_2$ and $R_3$ are joined together to form a 2 to 12 membered ring.

15. The method of claim 14 wherein $R_1$ is a hydroxyl group.

16. The method of claim 14 wherein $R_1$ is —$NR_2R_3$ where $R_2$ and $R_3$ are joined together to form a 2 to 12 membered ring with one or more of the cyclic atoms being a heteroatom.

17. The method of claim 14 wherein the ketoethanal compound comprises ethyl glyoxylate.

18. A method of producing an isomer of (3,6-dihydro-2H-pyran-2-yl)-methanol comprising the steps of:
    a) reacting 1,3-butadiene with a ketoethanal compound to form a racemic mixture of a 2-carbonyl-3,6-dihydropyran compound; and b) converting the 2-carbonyl-3,6-dihydropyran compound to (3,6-dihydro-2H-pyran-2-yl)-methanol, wherein the dihydropyran compound produced in step a) or the alcohol produced in step b) comprises a racemic mixture thereof and said method further comprises a step of resolving the racemic mixture such that the alcohol produced in step b) consists of one isomer thereof.

19. The method of claim 18 wherein the resolving step is performed between steps a) and b), said resolving step comprising treating the racemic mixture of the 2-carbonyl-3,6-dihydropyran compound with a hydrolase to produce a resolved product composition having an aqueous phase containing one isomer of (3,6-dihydro-2H-pyran-2-yl)-methanol and an organic phase containing the other isomer of (3,6-dihydro-2H-pyran-2-yl)-methanol.

20. The method of claim 18 wherein said resolving step comprises reacting one of the isomers of the racemic mixture of (3,6-dihydro-2H-pyran-2-yl)-methanol with a reaction compound in the presence of an enzyme to produce a mixture comprising a reaction product and the other isomer, the other isomer being unreacted.

21. The method of claim 20 wherein the reaction compound comprises vinyl acetate.

22. The method of claim 21 wherein the enzyme comprises lipase.

23. The method of claim 22 further comprising separating the unreacted isomer from the mixture.

24. The method of claim 18 wherein the 2-carbonyl-3,6-dihydropyran compound comprises a racemic mixture of an ester comprising 2-alkoxycarbonyl-3,6-dihydropyran and said resolving step comprises:

(i) hydrolyzing the ester to produce a racemic mixture of 3,6-dihydropyran-2-carboxylic acid;

(ii) treating the racemic mixture of 3,6-dihydropyran-2-carboxylic acid with a resolving agent to yield a mixture comprising one isomer of 3,6-dihydropyran-2-carboxylic acid and a reaction product of the other isomer;

(iii) reacting the isomer of 3,6-dihydropyran-2-carboxylic acid with an alcohol to produce an isomer of an ester; and (iv) reducing the ester of step (iii) to produce one isomer of (3,6-dihydro-2H-pyran-2-yl)-methanol.

* * * * *